(12) United States Patent
Wigren et al.

(10) Patent No.: US 10,371,595 B2
(45) Date of Patent: Aug. 6, 2019

(54) CONTROLLING A VACUUM SYSTEM COMPRISING A VACUUM GENERATOR ARRANGEMENT

(71) Applicant: Xerex AB, Täby (SE)

(72) Inventors: Gustaf Wigren, Vaxholm (SE); Peter Engborg, Skogås (SE)

(73) Assignee: Piab Aktiebolag, Taby (SE)

( * ) Notice: Subject to any disclaimer, the term of this patent is extended or adjusted under 35 U.S.C. 154(b) by 50 days.

(21) Appl. No.: 15/610,667

(22) Filed: Jun. 1, 2017

(65) Prior Publication Data

US 2017/0350784 A1 Dec. 7, 2017

(30) Foreign Application Priority Data

Jun. 1, 2016 (EP) .................... 16172446

(51) Int. Cl.
| | | |
|---|---|---|
| G01L 21/00 | (2006.01) | |
| G01M 3/28 | (2006.01) | |
| G01M 3/18 | (2006.01) | |
| G01M 3/32 | (2006.01) | |
| G05D 16/20 | (2006.01) | |
| F04F 5/20 | (2006.01) | |
| F04F 5/52 | (2006.01) | |
| G01N 1/14 | (2006.01) | |

(52) U.S. Cl.
CPC ............ *G01M 3/2876* (2013.01); *F04F 5/20* (2013.01); *F04F 5/52* (2013.01); *G01M 3/184* (2013.01); *G01M 3/3263* (2013.01); *G05D 16/2066* (2013.01); *G01L 21/00* (2013.01); *G01M 3/2815* (2013.01); *G01N 1/14* (2013.01)

(58) Field of Classification Search
CPC ............ G01M 3/2876; F04F 5/20; F04F 5/52
See application file for complete search history.

(56) References Cited

U.S. PATENT DOCUMENTS

| | | | | |
|---|---|---|---|---|
| 5,188,411 A | * | 2/1993 | Golden | ............ B65G 47/91 |
| | | | | 137/487.5 |
| 5,263,753 A | * | 11/1993 | Breu | ............ B25J 15/0206 |
| | | | | 294/196 |
| 5,617,338 A | * | 4/1997 | Sugano | ............ B65G 47/917 |
| | | | | 340/626 |

FOREIGN PATENT DOCUMENTS

| | | |
|---|---|---|
| DE | 42 29 834 A1 | 3/1993 |
| DE | 10 2011 118 173 A1 | 5/2013 |
| EP | 0 532 774 A1 | 3/1993 |
| GB | 2 326 696 A | 12/1998 |
| GB | 2326696 A * | 12/1998 ............ F04F 5/20 |
| WO | 2011/135450 A1 | 11/2011 |

* cited by examiner

*Primary Examiner* — Jamel E Williams
(74) *Attorney, Agent, or Firm* — Renner, Otto, Boisselle & Sklar, LLP

(57) ABSTRACT

The invention relates to energy saving in vacuum systems by means of a method and a controller enabling to consider the fluctuation in system-pressure of a system by determining a maximum system-pressure S2H and a minimum system-pressure S2$h$ for each working cycle $W_C$ based on a determined target system-pressure $p_n^-$ and a pre-set system-pressure $p_0^-$ for the current working cycle $W_{Cn}$ (n=1, 2, 3, . . . ). The method is especially adapted to fluctuations in system-pressure level of a vacuum system comprising a vacuum gripper tool.

14 Claims, 7 Drawing Sheets

CONTROLLING A VACUUM SYSTEM COMPRISING A VACUUM GENERATOR ARRANGEMENT

This application claims priority of European Application No. 16172446.3 filed Jun. 1, 2016 which is hereby incorporated herein by reference.

TECHNICAL FIELD

The present disclosure relates to a method of controlling, and a controller for a vacuum system comprising a vacuum generator arrangement driven by compressed air in order to generate a negative pressure applicable for suction cups or similar devices.

BACKGROUND

The present invention relates generally to material handling systems and, more particularly, to controlling a vacuum generator arrangement for suction cups of material handling systems that are engaged with the objects and substantially sealed thereto via operation of the vacuum system comprising the vacuum generator arrangement and the suction cups. It is known to provide a material handling system that includes suction cups or the like that are adapted to be moved into engagement with an object, such as a substantially flat object or panel or the like, and to lift and move the object to a desired location. The suction cups may be moved into engagement with the object, and the vacuum generator may be actuated to create a vacuum between the object and a suction cup such that the object is retained to the suction cup as it is transported to the desired location. Such material handling systems may be a part of one or more working stations.

The vacuum generated at the suction cup(s) is provided by the vacuum generator arrangement in the vacuum system, whereby pressurized air is supplied or provided to the vacuum generator of the arrangement.

When the air supply to the vacuum generator is deactivated, such that no vacuum is generated, the vacuum in the vacuum system may dissipate through a vent that connects the vacuum system to an atmosphere outside of the system, and when the vacuum has dissipated in the system and in the cup, to a sufficient amount, the suction cup may be released from the object.

Prior art devices are known from e.g. EP-1064464 where it is disclosed a vacuum ejector pump for generating a negative pressure used for transportation or lifting purposes. And in, U.S. Pat. No. 7,950,422 where it is disclosed an auto-release vacuum device for a material handling system.

Vacuum systems for transporting objects involve one or more vents for activating vacuum generation in a gripper tool. Such a vent is electrically opened, e.g. by solenoid, for letting air through the vacuum generator to generate vacuum pressure in the gripper. It is mechanically closed e.g. by a spring device or magnet, letting no air through to the vacuum generator when at least a preset vacuum pressure is achieved and/or no vacuum pressure should be generated. When the vent is closed, no electric power is consumed by the vent. The vacuum system may therefore involve an Energy Saving (ES) function for saving energy by not powering vents of the vacuum system. Thus, control signals are used by a vacuum system controller for controlling the Energy Saving (ES) function. Said ES function makes use of vacuum pressure level settings defining a pressure interval wherein vacuum generation is only active when a minimum pressure level is detected and it is necessary to increase vacuum pressure up to a preset maximum pressure level where the vacuum generation is stopped.

According to prior art, the setting of the minimum pressure level parameter, $ES_{Low}$, and maximum pressure level, $ES_{High}$, is performed manually by an operator or user of a working station and it requires that the operator to take into consideration any fluctuation of the vacuum pressure over time in the gripper application that will affect the ability of the vacuum generator to reach a system vacuum pressure, i.e. system-pressure, $p_n^-$ equal to or higher than $ES_{High}$.

Thus, one drawback is that an operator has to set the threshold values $ES_{Low}$ and $ES_{High}$ manually for any gripper tool application of the working station. Further one drawback, or problem, is that the operator has to be very skilled and experienced to be able to set the threshold values $ES_{Low}$, and $ES_{High}$ and to consider any fluctuation of the vacuum generation and pressure over time and many repeating working cycles $W_C$ in the gripper application.

The object of the present invention is to achieve an improved vacuum system that eliminates, or at least mitigates, the above stated drawbacks, by being more user-friendly to handle.

SUMMARY

One object of the present invention is to provide a method, control unit and vacuum system for controlling a vacuum generator arrangement that eliminates, or at least mitigates, the above stated drawbacks.

The above-mentioned object is achieved by the present invention according to the aspects and embodiments of the independent claims. Preferred embodiments are set forth in the dependent claims.

According to an aspect, it is provided a method for automatic pressure level determination and adaptation. Said method enables energy saving in working cycles in a vacuum system operating a vacuum gripper tool for transportation of objects. Said vacuum system comprises a vacuum generator arrangement driven by a compressed air flow. The vacuum generator arrangement via a vacuum chamber being part of the vacuum system is arranged to be brought in flow connection with the vacuum gripper tools, in order to supply vacuum to the vacuum gripper in result of the compressed air flow. A pressure sensor for monitoring a system-pressure $p^-(t)$ is arranged inside the vacuum chamber. A vacuum system controller is electrically connected to a main controller, wherein the vacuum system controller is arranged to control and communicate with the vacuum generator arrangement and communicate with the pressure sensor. The vacuum system controller is arranged to monitor the measured system-pressure $p^-(t)$ continuously, characterized in that the vacuum system controller further is capable to calculate the system-pressure time derivative $D(t)=dp^-/dt$ during the working cycles. The method comprises determining at start-up of a working cycle value $D_0$ of the system-pressure time derivative at a pre-set system-pressure $p_0^-$, calculating value $D_{target}$ of target system-pressure time derivative using the value $D_0$; comparing the system-pressure time derivative $D(t)$ to $D_{target}$ until $D(t)$ equals $D_{target}$, and determining a target system-pressure $p_n^-$ where $D(t)$ equals $D_{target}$. The method further comprises calculating the maximum system-pressure S2H and the minimum system-pressure S2h by means of the target system-pressure $p_n^-$ and the pre-set system-pressure $p_0^-$ and operating the vacuum generator arrangement to reestablish a vacuum system-pressure $p^-(t)$ to maximum system-pressure S2H when the vacuum system-pressure $p^-(t)$ is equal to or closely equal to the minimum system-pressure S2h.

According to another aspect, there is provided a controller for automatic pressure level determination and adaptation enabling energy saving in working cycles in a vacuum system operating a vacuum gripper tool for transportation of objects. Said vacuum system comprises a vacuum generator arrangement driven by a compressed air flow. The vacuum generator arrangement via a vacuum chamber being part of the vacuum system is arranged to be brought in flow connection with the vacuum gripper tools, in order to supply vacuum to the vacuum gripper in result of the compressed air flow. A pressure sensor for monitoring a vacuum system-pressure $p^-(t)$ is arranged inside the vacuum chamber. A vacuum system controller is electrically connected to a main controller, wherein the vacuum system controller is arranged to control and communicate with the vacuum generator arrangement and communicate with the pressure sensor. The vacuum system controller is configured to monitor the measured system-pressure $p^-(t)$ continuously, characterized in that the vacuum system controller further is capable to calculate the system-pressure time derivative $D(t)=dp^-/dt$ during the working cycles. Said controller comprises a processor in a processing circuitry being operative of determining at start-up of a working cycle value $D_0$ of the system-pressure time derivative at a pre-set system-pressure $p_0^-$, calculating value $D_{target}$ of target system-pressure time derivative using the value $D_0$, comparing the system-pressure time derivative $D(t)$ to $D_{target}$ until $D(t)$ equals $D_{target}$, and determining a target system-pressure $p_n^-$ where $D(t)$ equals $D_{target}$. The vacuum system controller is further configured to calculate the maximum system-pressure S2H and the minimum system-pressure S2h by means of the target system-pressure $p_n^-$ and the pre-set system-pressure $p_0^-$ and operate the vacuum generator arrangement to reestablish a vacuum system-pressure $p^-(t)$ to maximum system-pressure S2H when the vacuum system-pressure $p^-(t)$ is equal to or closely equal to the minimum system-pressure S2h.

According to another aspect, there is provided a vacuum system for transportation of objects, said system comprising a controller a specified above.

The invention, according to the various aspects and embodiments, solves the problem, which is frequently encountered in, but not limited to, applications with working stations and ergonomic lifting devices having a gripper with suction cups and equipped with energy saving possibilities.

Yet another object of the invention is to provide a vacuum system comprising an energy saving function which can be adapted to varying demands for air in order to interrupt the vacuum in a vacuum gripper tool.

SHORT DESCRIPTION OF THE DRAWINGS

The invention is explained more in detail below with reference made to the accompanying drawing, wherein embodiments of the invention are illustrated schematically:

DETAILED DESCRIPTION OF THE INVENTION

Figure 1:
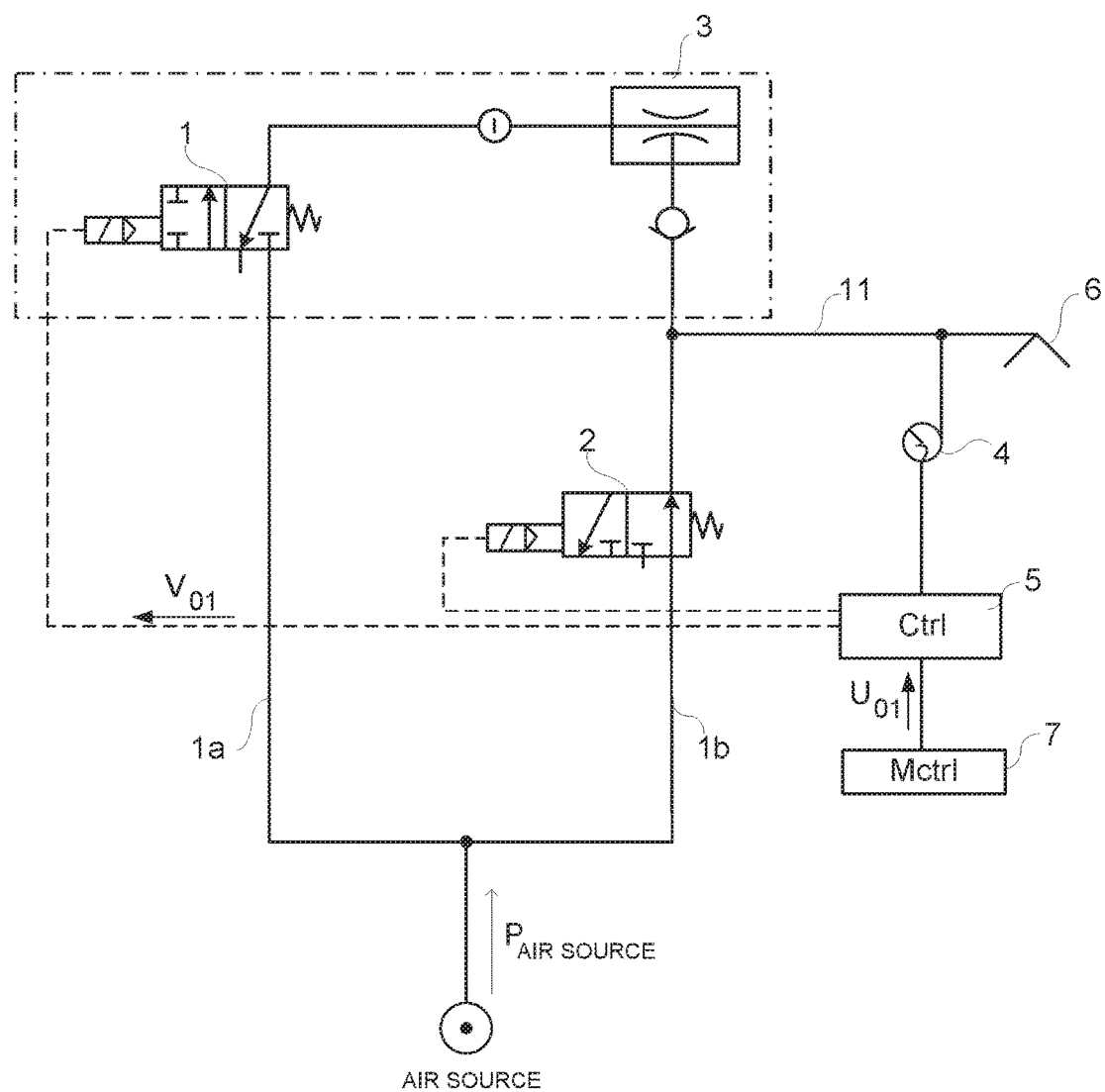
FIG. 1 is a block diagram illustrating a schematic view of a vacuum system 10 according to prior art.

For a general description of implementation of a vacuum system 10 for transportation of objects, reference is initially made to FIG. 1.

Herein the term "vacuum gripper" or "vacuum gripper tool" is alternately used, but the two terms refers to the same kind vacuum gripping means, which also may include a plurality of vacuum grippers.

The vacuum system 10 comprises a vacuum generator 3 driven by a compressed air flow via a first on/off valve 1, or other means for controlling the compressed air flow, wherein the vacuum generator 3 via a vacuum chamber 11 being part of the vacuum system 10 is arranged to be brought in flow connection with one or more vacuum grippers 6 comprised in the vacuum system 10, in order to supply vacuum to the vacuum gripper 6 in result of the compressed air flow to the vacuum generator 3. The vacuum system 10 comprises a second valve 2 arranged to supply compressed air into the vacuum system 10. In FIG. 1, the line $P_{air\ source}$ represents the direction of compressed air flow from a compressed air supply source AIR SOURCE via the first valve 1 to the vacuum generator 3. The air supply source AIR SOURCE is typically the same both for supplying compressed air to the vacuum generator 3, in other words to the first valve 1, as well as to the second valve 2 for allowing compressed air into the system 10, typically inside a vacuum chamber 11, but via different supply connections 1a and 1b as illustrated in the figure.

A pressure sensor 4 is provided inside, or at, or centrally located to, the vacuum chamber 11 for monitoring a system-pressure $P=p^-(t)=p^-$. The vacuum system 10 further comprises a vacuum system controller 5, also referred to as a "controller". As an example, but without any limitation thereto, the valves 1 and 2 can either be directly operated solenoid-valves, or operating as pilot-valves to actuate piloted valves to supply the vacuum generator and/or vacuum system 10 with air.

Typically, the controller 5 is arranged to communicate with the first on/off valve 1 via signaling $V_{01}$, the second valve 2 and the pressure sensor 4. The vacuum system 10, and/or the vacuum generator 3 can be integrated with the controller 5 and the control-valves 1 and 2, as well as the system-pressure sensor 4 (sometimes also referred to as a pressure gauge), of which the latter can be used to monitor the system-pressure $P=p^-$ in the vacuum system, in particular in the vacuum chamber 11. The controller 5 is monitored and controlled by a main controller 7 via signaling $U_{01}$, which is the vacuum control signal to controller 5 from main controller. The signal $V_{01}$ is the internal vacuum control signal to the first on/off valve 1. The values of the signals $U_{01}$ and $V_{01}$ may be binary, e.g. either "1" or "0", i.e. "one" or "zero". Signal levels "1" and "0", respectively, may be interpreted as "true" or "false". Thus, if "1" is set to "true" than "0" is set to "false", or if "1" corresponds to "false"

than "0" corresponds to "true". Further, signal value "1" may be characterized as "high" and signal value "0" may be characterized as "low". In addition, other values than "1" and "0" may be used, e.g. "1" and "−1", "0" and "−1", etc.

If, for example, signal $U_{01}$ is "high" from main controller 7 to controller 5, this means that the gripper tool 6 should be activated for attaching by suction to an object to be lifted. If, on the contrary, signal $U_{01}$ is "low" from main controller 7 to controller 5, this means that the gripper tool 6 should be deactivated for releasing the object to which the vacuum gripper tool is attached. Thus, the main controller 7 controls the attachment or release of the vacuum gripper tool to an object via the controller 5. The controller 5 controls the first on/off valve 1, second valve 2, and vacuum generator 3, but also other parts of the vacuum system.

The controller 5 may be defined and/or operated by components including a specific control-algorithm implemented in an existing controller used for controlling the first on/off valve 1, second valve 2, and vacuum generator 3, but also other parts of the vacuum system.

When the on/off valve 1 is not flowing air to the vacuum generator 3, and the controller 5 indicates a state of no vacuum generation, for instance by a signal $V_{01}$ to the first valve 1, or to the vacuum generator per se, and if a fluctuation from a pressure-equilibrium to a negative time-derivative of the system-pressure P is detected, for example if vacuum is detected at the vacuum grippers 6 or inside the vacuum chamber 11, the controller 5 is arranged to activate the second valve 2, allowing an amount of compressed air to flow into the vacuum-chamber 11 for compensation to re-establish the pressure-equilibrium, such that there is no negative pressure but atmospheric pressure as intended.

In this way, the second valve 2 provides a vacuum gripper 6 with immediate supply of air for an active release of an object gripped by the vacuum gripper 6. Herein the term "vacuum gripper" also includes a plurality of vacuum grippers and vacuum gripper tool.

As is understood by the description of FIG. 1, a working cycle starts when the vacuum gripper tool has been applied to the object, and it ends when the object has been released.

Figure 2:
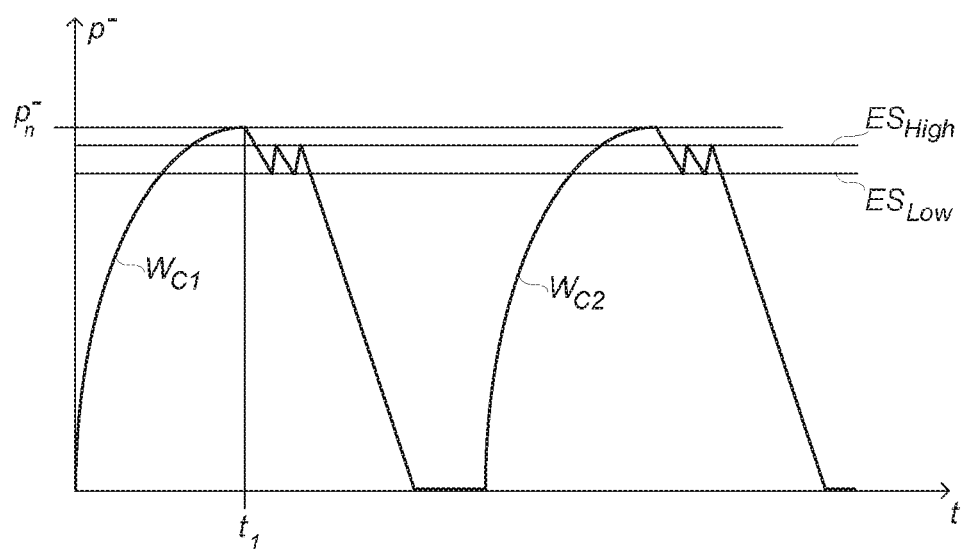
FIG. 2 is a pressure over time diagram illustrating working cycles in a vacuum system.

FIG. 2 is a pressure over time diagram illustrating the working cycles for a vacuum gripper.

When a new working cycles $W_{C1}$ for the vacuum gripper tool starts, the controller activates the vacuum generation and the system system-pressure P=p⁻ rises from null, "0", up to system-pressure P=$p_n^-$ at the time $t_1$. The vacuum generation stops by the controller closing the first on/off valve at system-pressure P=$p_n^-$ resulting in that the air flow from the air source through the first on/off valve is shut off. This time is indicated as $t_1$. The system-pressure P=p⁻ will sink due to leakage in the system, especially in the vacuum gripper tools. When the system-pressure has sunken to p⁻=$ES_{Low}$ the first on/off valve is opened by the controller and the system-pressure p⁻ generation in the vacuum chamber starts and rises to p⁻=$ES_{High}$ where the vacuum generation stops by shutting the air flow from the air source through the first on/off valve off. The leakage in the system and the gripper tools will again result in the sink of the system-pressure p⁻ when the system-pressure has sunken to p⁻=$ES_{Low}$ the first on/off valve is opened again by the controller and the system-pressure p⁻ generation in the vacuum chamber starts and rises to p⁻=$ES_{High}$ where the vacuum generation stops by shutting the air flow through the first on/off valve from the air source to the vacuum generator off. This repetition process comprising to let the system-pressure p⁻ sink to p⁻=$ES_{Low}$ and to start the system-pressure p⁻ generation in the vacuum chamber to rise the system-pressure p⁻=$ES_{High}$ is repeated until the controller sends a release control signal for releasing the vacuum gripper tool from the transported object. The release control signal makes the system-pressure p⁻ to sink to null, "0", by letting air into the grippers. When the gripper tool has released the object at the end of the transportation path of a working station, the main controller guides the gripper tool back to the beginning, or start, of the transportation path. A new working cycles $W_{C2}$ for the vacuum gripper tool starts.

The pressure sensor transduces measured vacuum pressure p⁻ to electrical signals which values are dependent of the measured system-pressure p⁻.

Figure 3:
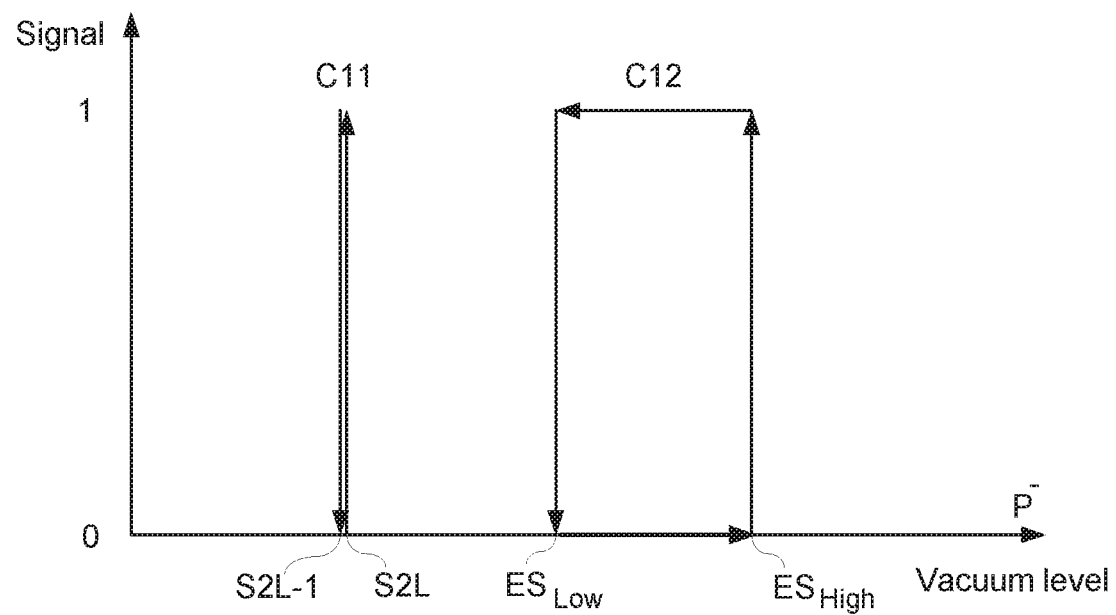
FIG. 3 is a diagram illustrating the vacuum based control signals C11 and C12 used in prior art.

FIG. 3 is a diagram illustrating the vacuum based control signals C11 and C12 as a function of system-pressure according to known prior art. C11 and C12 are vacuum level based control signals. The control signal C11 is based on two system-pressure levels indicated as S2L-1 and S2L in the diagram. The control signal C12 is based on two system-pressure levels indicated as $ES_{Low}$ and $ES_{High}$. In the following example, the values of the signals C11 and C12 are binary, e.g. either "1" or "0", i.e. "one" or "zero". Signal levels "1" and "0", respectively, may be interpreted as "true" or "false". Thus, if "1" is set to "true" than "0" is set to "false", or if "1" corresponds to "false" than "0" corresponds to "true". Further, signal value "1" may be characterized as "high" and signal value "0" may be characterized as "low". In addition, other values than "1" and "0" may be used, e.g. "1" and "−1", "0" and "−1", etc.

Normally, there is a control signal C11 present in the vacuum system which is used as a "ready" signal for higher level control systems, such as the main controller (7 in FIG. 1), of the working station. In the illustrated example of FIG. 3, the control signal C11 is set to 1 for measured system-pressure p⁻ for each system-pressure p⁻ larger than but less or equal to p⁻=s2L. For system-pressure values p⁻ less or equal to p⁻=s2L-1 or larger than p⁻=s2L, C11=0, i.e. C11 is set to zero. Thus, C11 is set to "1"/high/true within a defined and specified system-pressure interval and to "0"/low/false outside said interval.

The control signal C12 is set to 1 when the measured system-pressure p⁻ equals p⁻=$ES_{High}$ and sinks down to and equals p⁻=$ES_{Low}$. For system-pressure values if less than p⁻=$ES_{Low}$ or larger than p⁻=$ES_{High}$, C12=0, i.e. C12 is set to zero. Thus, C12 is set to "1"/high/true within a defined and specified system-pressure interval when the system-pressure p⁻ sinks and to "0"/low/false outside said interval or when the system-pressure p⁻ is raising even though the pressure p⁻ is within said value. During a working cycle when $U_{01}$ is "true", the controller turns the compressed air to the ejector off automatically when a specific vacuum level is achieved, C12 is "1", or true. This will save energy, as the vacuum generator now does not consume any energy to maintain an acceptable system-pressure level p⁻, equal or higher than $ES_{Low}$, of the system (10 in FIG. 1). If the vacuum level drops below $ES_{Low}$, where C12 turns to "0" (or false), the compressed air is turned back on.

Thus, control signals C11 and C12 are used by the controller 5 for controlling the Energy Saving (ES) function.

According to prior art, the setting of signal C12 and setting of the pressure interval values $ES_{High}$ and $ES_{Low}$ is performed manually by an operator or user of a working station and it requires that the operator to take into consideration, any fluctuation of the system-pressure over time in the gripper application that will affect the ability of the vacuum generator to reach a system-pressure p⁻ equal to or higher than $ES_{High}$.

Thus, one drawback is that an operator has to set the parameter values $ES_{Low}$ and $ES_{High}$ manually for any gripper tool application of the working station. Further one drawback, or problem, is that the operator has to be very skilled and experienced to be able to set the threshold values $ES_{Low}$ and $ES_{High}$ and to consider any fluctuation of the vacuum generation and pressure over time and many repeating working cycles $W_C$ in the gripper application.

Figure 4:
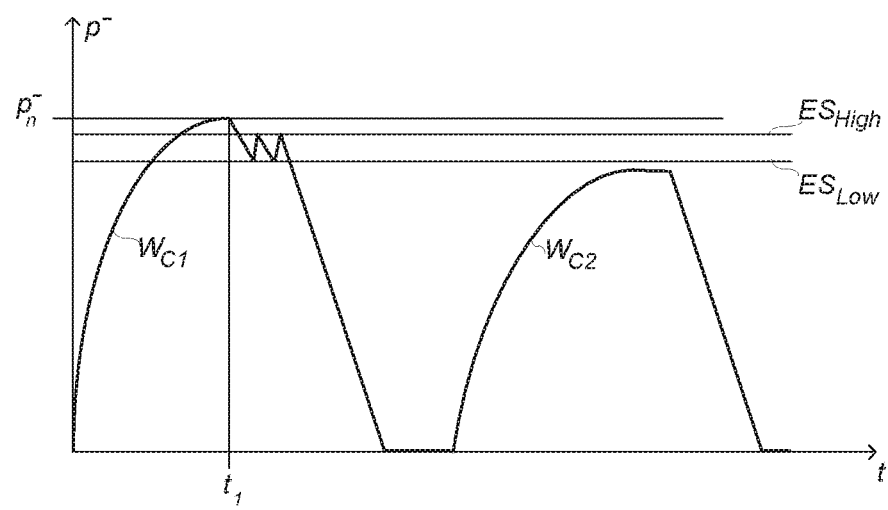
FIG. 4 is a pressure over time diagram illustrating one problem with prior art.

FIG. 4 is a pressure over time diagram illustrating working cycles for a vacuum gripper.

FIG. 4 illustrates another drawback that may occur during an operation process of a working station. As the threshold values $ES_{Low}$, and $ES_{High}$ are set manually, the setting is not adjusted to fluctuations of the vacuum generation and pressure during each working cycle $W_C$. If the user has chosen non-reachable settings for C12 or even C12 is not present in the system, energy savings will not be possible in all working cycles. In the example of FIG. 4, the threshold values $ES_{Low}$ and $ES_{High}$ are set manually and for the first working cycle $W_{C1}$ the set threshold values are appropriate. However, due to fluctuations of the vacuum generation, the system-pressure in the vacuum chamber and gripper tool for the second working cycle $W_{C2}$ will not be as high as in the first working cycle. The system-pressure will not reach the threshold values $ES_{Low}$ and $ES_{High}$, which will result in that no energy saving will occur for such a working cycle.

The present application addresses at least one of said drawbacks, or problems, by providing an Automatic Level Determination (ALD) function to a working station using vacuum gripper tools. Said ALD function makes use of a control signal C13. When the control signal $U_{01}$ from the main controller is $U_{01}=1$ (true or high), the Energy Saving function is executed based on control signals C11 and C13. The state (true or false) of the control signal $V_{01}$ from the vacuum system controller is controlled by an algorithm of the ALD function, which algorithm calculates threshold values S2H and S2h for the signal C13 dynamically.

Thus, a solution to are provided arrangement and a method for energy saving using automatic adaptation to system-pressure levels of working cycles ($W_C$) in a vacuum system operating vacuum gripper tools for transportation of objects.

Figure 5:
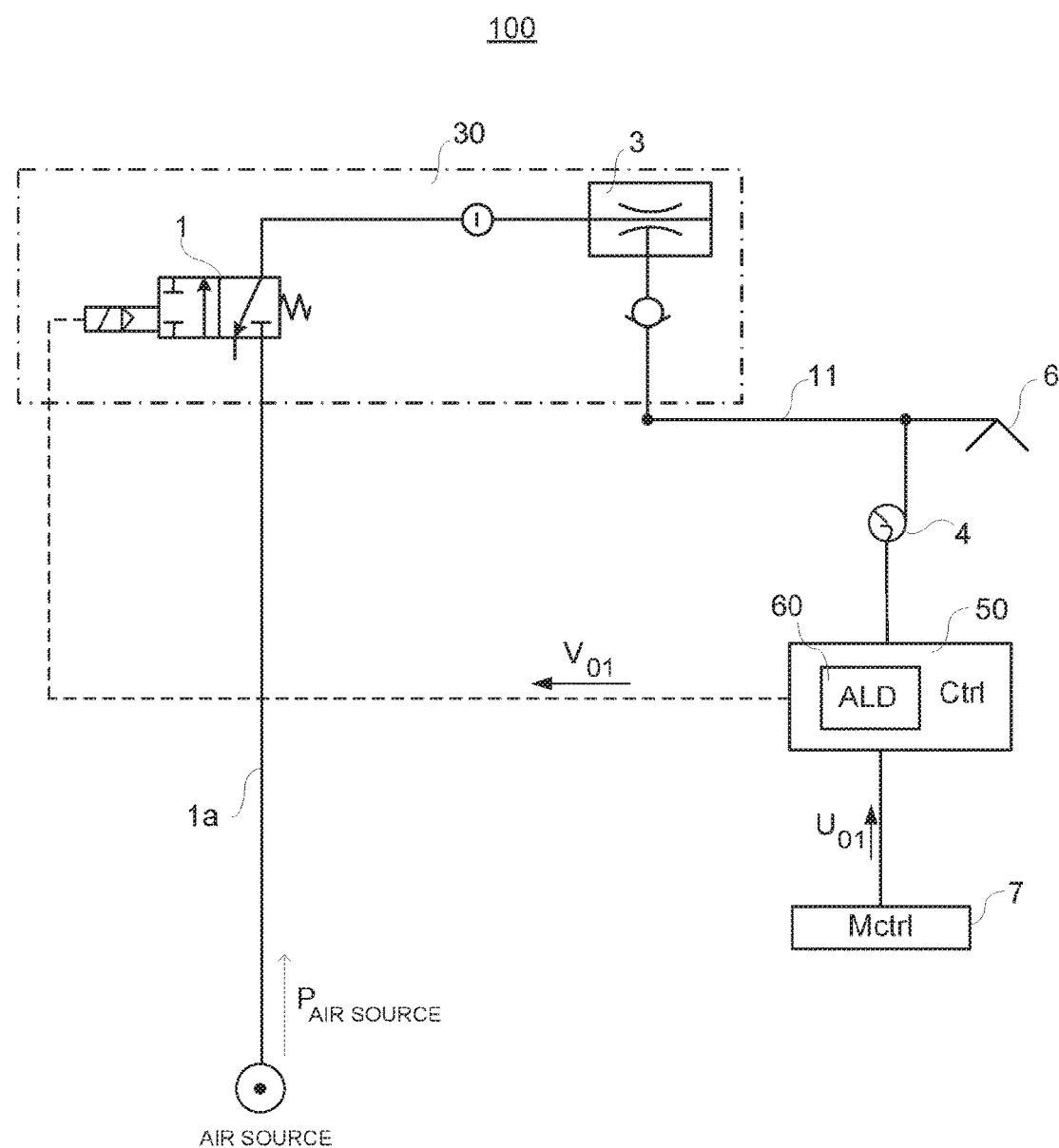
FIG. 5 is a schematic view of a vacuum system 100 according to the invention.

FIG. 5 is a schematic view of a vacuum system 100 according to the invention.

An embodiment of the invention will now be described with reference to FIG. 5, wherein details of the embodiment that correspond to the above description of the vacuum system will be indicated by the corresponding reference numbers that were previously used in FIG. 1. For a general description of implementation of a vacuum system 10 for transportation of objects reference is initially made to FIG. 1.

The vacuum system 100 comprises a vacuum generator arrangement 30 driven by a compressed air flow via one supply connection 1a. The vacuum generator arrangement 30 comprises a vacuum generator 3 comprises a first on/off valve 1, or other means for controlling the compressed air flow. The vacuum generator and the valve 1 may be designed as one unit 30, as illustrated in FIG. 5. According to another embodiment, the vacuum generator 3 and the valve 1 may be designed as separate parts of the vacuum generator arrangement 30. Thus, the design of the vacuum generator arrangement 30 is not limited to illustrated embodiment in FIG. 5. The vacuum generator 3 may be realized as a vacuum ejector. The vacuum system 100 further comprises a vacuum chamber 11, which is arranged to be brought in flow connection with one or more vacuum grippers 6 comprised in the vacuum system 100. The compressed air flow through the vacuum generator 3 results in vacuum pressure in the vacuum gripper 6. The vacuum system 100 may comprise a second valve that is arranged to supply compressed air into the vacuum system 100. In FIG. 5, the line $P_{air\ source}$ represents the direction of compressed air flow from a compressed air supply source AIR SOURCE via the on/off valve 1 in the vacuum generator 3.

A pressure sensor 4 is provided inside, or at, or centrally located to, the vacuum chamber 11 for monitoring a system pressure $P=p^-(t)$. The vacuum system 100 further comprises a vacuum system controller 50, also referred to as a "controller" for operating and controlling the vacuum generator 3. As an example, but without any limitation thereto, the vacuum generator 3 may be directly controlled via the valve 1. Said valve 1 can either be a directly operated solenoid-valve, or operating as pilot-valve to actuate the piloted valve to supply the vacuum generator and/or vacuum system 100 with air.

Typically, the controller 50 is arranged to communicate with the on/off valve 1 via signaling $V_{01}$, and the pressure sensor 4. The vacuum system 100, and/or the vacuum generator arrangement 30 can be integrated with the controller 50 and the control-valve 1, as well as the system-pressure sensor 4 (sometimes also referred to as a pressure gauge), of which the latter can be used to monitor the system vacuum pressure, system-pressure P in the vacuum system, in particular in the vacuum chamber 11. The controller 50 is monitored and controlled by a main controller 7 via signaling $U_{01}$, which is the vacuum control signal to controller 50 from main controller. The signal $V_{01}$ is the internal vacuum control signal to the vacuum generator or the on/off valve 1 of the vacuum generator arrangement 30. The values of the signals $U_{01}$ and $V_{01}$ are preferably binary, e.g. either "1" or "0", i.e. "one" or "zero". Signal levels "1" and "0", respectively, may be interpreted as "true" or "false". Thus, if "1" is set to "true" than "0" is set to "false", or if "1" corresponds to "false" than "0" corresponds to "true". Further, signal value "1" may be characterized as "high" and signal value "0" may be characterized as "low". In addition, other values than "1" and "0" may be used, e.g. "1" and "−1", "0" and "−1", etc.

If, for example, signal $U_{01}$ is "high" from main controller 7 to controller 50, this means that the gripper tool 6 should be activated for attaching by suction to an object to be lifted. If, on the contrary, signal $U_{01}$ is "low" from main controller 7 to controller 50, this means that the gripper tool 6 should be deactivated for releasing the object to which the vacuum gripper tool is attached. Thus, the main controller 7 controls the attachment or release of the vacuum gripper tool to an object via the controller 50. The controller 50 controls the on/off valve 1, and the vacuum generator 3, but also other parts of the vacuum system.

The controller 50 may be defined and/or operated by components including a specific control-algorithm implemented in an existing controller used for controlling the on/off valve 1 of the vacuum generator arrangement 30, but also other parts of the vacuum system.

The controller 50 indicates a state of no vacuum generation, for instance by a signal $V_{01}$ to the vacuum generator per se, or the on/off valve 1 of the vacuum generator arrangement 30. In this way, the second valve 2 provides a vacuum gripper 6 with immediate supply of air for an active release of an object gripped by the vacuum gripper 6.

According to the invention, said vacuum system controller 50 is equipped with an Automatic Level Determination, ALD, function indicated as a box having reference number 50. Said ALD function enables the controller 50 to perform a method S100 for energy saving in a vacuum system 100 using automatic determination of and adaptation to system-pressure levels of working cycles in the vacuum system 100 operating one or more vacuum gripper tools for transportation of objects of a working station. The vacuum system controller is arranged to monitor and control system-pressure $P=p^-(t)=p^-$ and to determine an energy saving system-pressure interval defined by a maximum system-pressure S2H and a minimum system-pressure S2$h$, wherein the maximum system-pressure S2H corresponds to the manually set $ES_{High}$ and minimum system-pressure S2$h$ corresponds to the manually set $ES_{low}$. Said method S100 is illustrated in FIG. 6.

Figure 6:
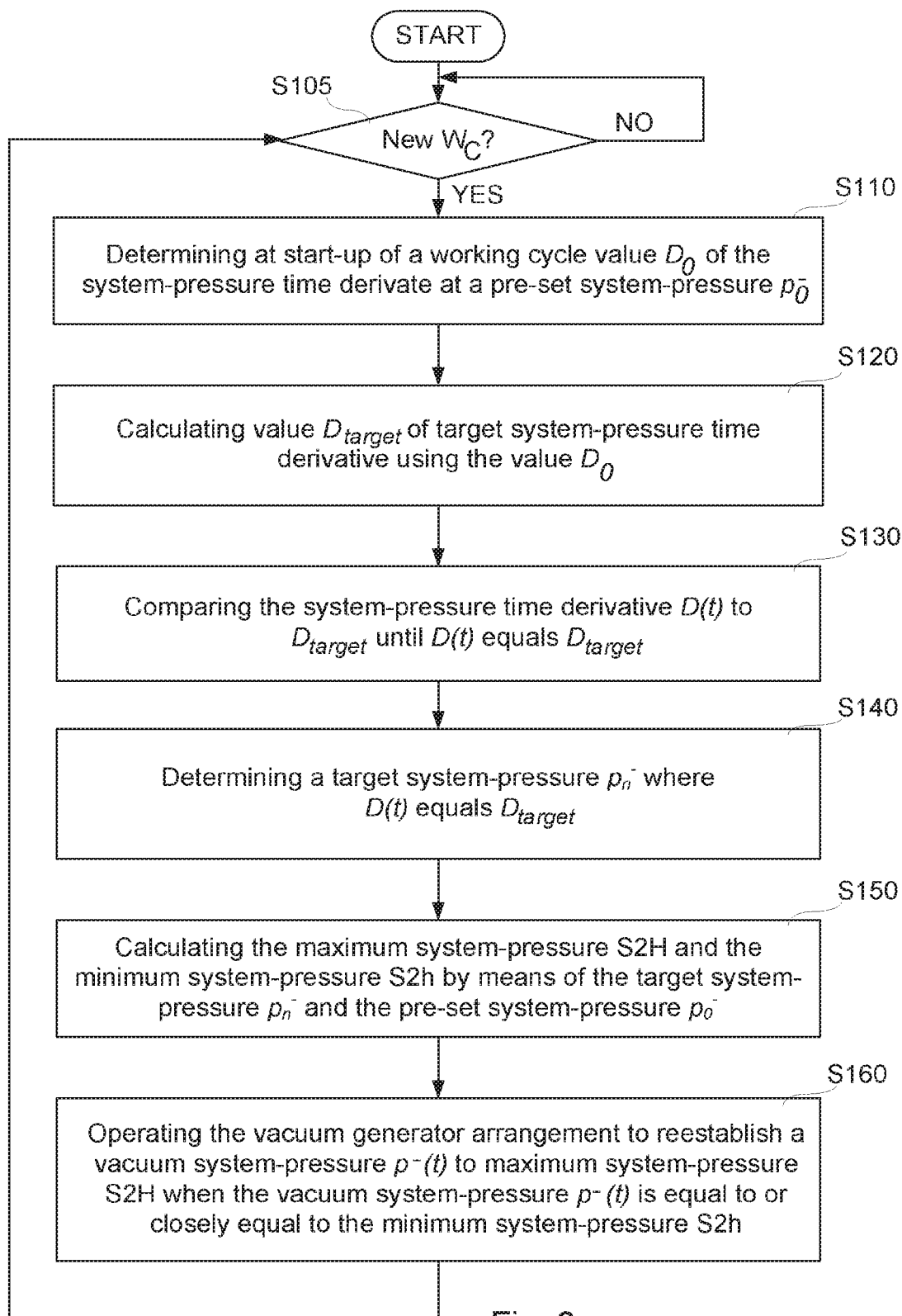
FIG. 6 is a flowchart of a method for automatic level determination and adaptation according to the invention.

FIG. 6 is a flowchart of a method for automatic level determination (ALD) and adaptation according to the invention. The method enables energy saving in during the working cycles in a vacuum system comprising and operating a vacuum generator arrangement. Such systems are described both in FIG. 1 and FIG. 5. The method may be implemented as executable computer program instructions in computer program software, or as hardware. Said computer program software will cause a programmable logic computer to perform the steps of the method when run in and by a programmable logic computer, PLC. The above described vacuum system controller (50 in FIG. 5) is a programmable logic computer. The method, or ALD function, may be carried out by the vacuum system controller, or another PLC that is able to communicate with said controller constituting vacuum system controller arrangement. The vacuum system controller is arranged to control and communicate with the vacuum generator arrangement and with a pressure sensor for measuring system-pressure $P=p^-(t)$ $=p^-$. The controller is arranged to monitor the measured system-pressure $p^-$ continuously. The controller is further capable to calculate the system-pressure time derivative $D(t)=dp^-/dt$ during working cycles.

The method S100 may comprise following steps:

S110: Determining at start-up of a working cycle value $D_0$ of the system-pressure time derivative at a pre-set system-pressure $p_0^-$;

S120: Calculating value $D_{target}$ of target system-pressure time derivate using the value $D_0$;

S130: Comparing the system-pressure time derivative $D(t)$ to $D_{target}$ until $D(t)$ equals $D_{target}$;

S140: Determining a target system-pressure $p_n^-$ when $D(t)$ equals $D_{target}$;

S150: Calculating the maximum system-pressure S2H and the minimum system-pressure S2$h$ by means of the target system-pressure $p_n^-$ and the pre-set system-pressure $p_n^-$;

S160: Operating the vacuum generator arrangement to reestablish a vacuum system-pressure $p^-(t)$ to maximum system-pressure S2H when the vacuum system-pressure $p^-(t)$ is equal to or closely equal to the minimum system-pressure S2$h$.

The method is repeated automatically for each new working cycle of the vacuum system. In one embodiment of the method, the method may set the PLC in a waiting or stand-by mode. Said method may therefor comprise a step:

S105: New $W_C$?

The method steps of S100 will now be explained in more details with reference to FIGS. 7 and 8.

Figure 7:
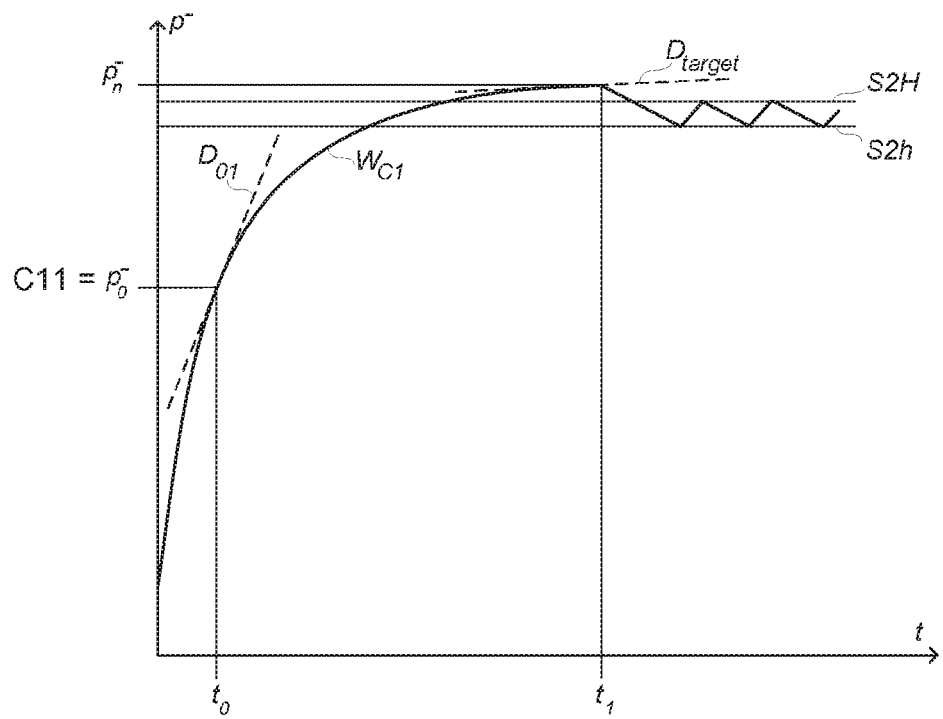
FIG. 7 is a diagram illustrating the pressure level determination and settings for a working cycle $W_{C1}$.
Figure 8:
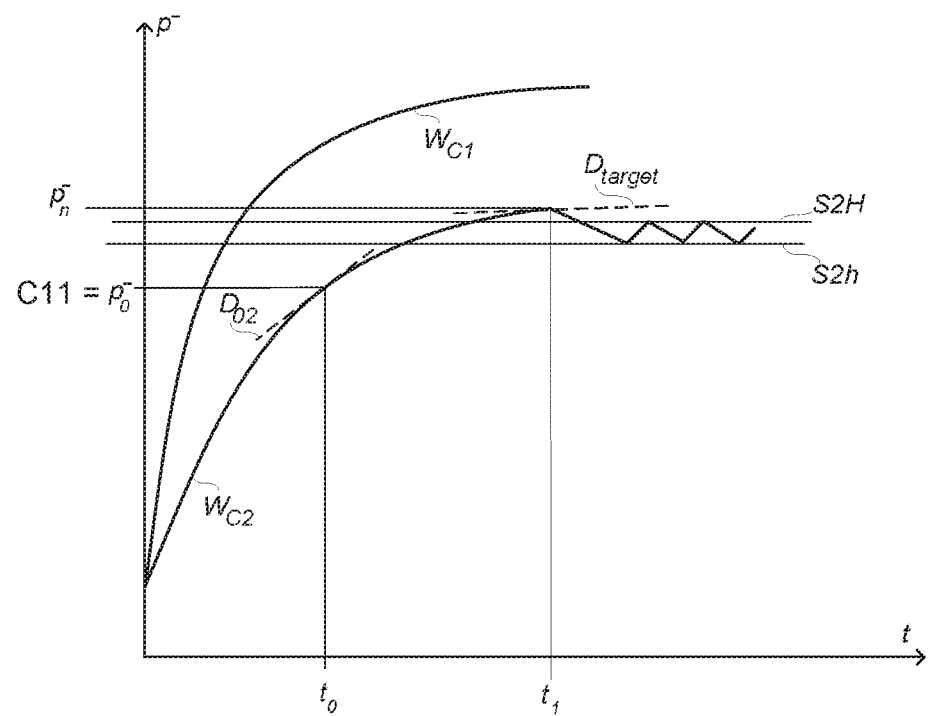
FIG. 8 is a diagram illustrating the pressure level determination and settings for another working cycle $W_{C2}$.

FIGS. 7 and 8 are diagrams illustrating curves $W_{C1}$, $W_{c2}$ of vacuum system pressure $p^-$ as a function of time. The curves belong to two different working cycles $W_{C1}$ and $W_{C2}$. The vacuum system controller 5 is arranged to monitor system-pressure continuously and to determine for the working cycles $W_C$ of the vacuum gripper tool an energy saving system-pressure interval defined by a maximum system-pressure S2H and a minimum system-pressure S2$h$.

In FIG. 7, a working cycle $W_{C1}$ is started up and the vacuum pressure in the system rises. At a pre-set system-pressure, $C11=p^-(t=t_0)=p_0^-$ the change of system-pressure over time, $D_0$, is measured and calculated in step S110. The change of system-pressure over time is the inclination of the tangent, $D_{01}$, of the system-pressure time derivative $dp/dt$ at $p^-=p_0^-=C11$. The value of the inclination $D_{01}$ can be determined by using numerical methods. As the system pressure sensor (4 in FIG. 5) measures the rise of system-pressure $p^-(t)$ both before and after $P=p_0^-=C11$. By measuring and registering the $p^-(t)$ values in a number of points before and after $p_0^-=C11$, said values may be used in a well-known numerical algorithm for calculating derivatives. Said derivative $D_0$ is then used in step S120 for calculating a value $D_{target}$ of the target system-pressure time derivative using the value $D_0$ (in this example $D_{01}$) at the pre-set system-pressure $p_0^-$. $D_{target}$ may be calculated by multiplying an appropriate pre-selected coefficient k less than one, i.e. "1":

$$D_{target}=k*D_0 \qquad (Eq. 1),$$

wherein $0<k<1$.

The value $D_{target}$ is then used in S130 for comparing system-pressure time derivative $D(t)$ to $D_{target}$ during the rise of system-pressure until $D(t)$ equals $D_{target}$ In step S140, target system-pressure $p_n^-$ is determined by measuring and selecting the measured value $p_n^-$ when $D(t)$ equals $D_{target}$ The time is indicated as $t=t_1$.

According to the invention, in step S150, it is suggested to calculate a maximum system-pressure S2H and a minimum system-pressure S2$h$ by means of the target system-pressure $p_n^-$ and the pre-set system-pressure $p_0^-$. The maximum system-pressure S2H may be calculated by using the equation $$S2H=p_0^-+(p_n^- -p_0^-)*K_1 \qquad (Eq. 2)$$

where $K_1$ is set according to a value $0.5 \leq K_1 < 1.0$

The minimum system-pressure S2$h$ is calculated by using the equation $$S2h=p_n^- -(p_n^- -S2H)*K_2 \qquad (Eq. 3)$$

where $K_2$ is set to a value $0<K_2 \leq 20$.

The vacuum system controller 5 is now able to perform step S160, wherein the vacuum generator arrangement is controlled and operated within an energy saving system-pressure interval defined by a maximum system-pressure S2H and a minimum system-pressure S2$h$ according to an operation condition stating to reestablish a vacuum system-pressure $p^-(t)$ to maximum system-pressure S2H when the vacuum system-pressure $p^-(t)$ is equal to or closely equal to the minimum system-pressure S2$h$. With closely is meant±5% of S2$h$. Thus, the vacuum generator arrangement is closed by setting $V_{O1}$ to the binary value corresponding to "off" if $p^-(t) \geq S2H$, and if $p^-(t) \leq S2h$ starting the vacuum generation arrangement in the vacuum system by setting $V_{O1}$ to the binary value corresponding to "on" wherein the vacuum generator arrangement is open letting air through it.

In FIG. 7, said operation condition is illustrated for the working cycle $W_{C1}$. At time $t=t_1$ the target system-pressure $p_n^-$ is reached where the system-pressure time derivative equals the target system-pressure time derivative value $D_{target}$. The vacuum system controller sets $V_{O1}$ to the binary value corresponding to "off" thereby closing the vacuum generator arrangement, e.g. on/off valve of the vacuum generator arrangement, and the system-pressure $p^-(t)$ will sink. When $p^-(t)$ has sunken to $p^-(t) \leq S2h$, the controller sets $V_{01}$ to the binary value corresponding to "on" wherein the vacuum generator arrangement is open, and the system-pressure rises again till $p^-(t) > S2H$, where the vacuum system controller sets $V_{01}$ to the binary value corresponding to "off" thereby closing the air flow thru the vacuum generator arrangement by means of the on/off valve, and the system-pressure $p^-(t)$ will sink. This operation will be repeated until the control signal $U_{01}$ from the main controller to the vacuum system controller is set to the binary value corresponding to "release" vacuum gripper. The system-pressure than falls to "zero" and the station is ready for a new working cycle. In step 105, the vacuum system controller is in a stand-by mode waiting for a new working cycle to start. Thus, the steps of the method S100 are repeated for each new working cycle.

One advantage of the invention over prior art will now be described with reference to FIG. 8. The system-pressure curves for two working cycles $W_{C1}$ and $W_{C2}$ are illustrated. The method and the pressure curve $W_{C1}$ were described above. In one of the following working cycles $W_{C2}$, the vacuum system-pressure $p^-(t)$ may not rise as in the previous working cycle $W_{C1}$ and the target system-pressure $p_n^-$ may be lower. This circumstance will be detected at the pre-set system-pressure, $C11 = p_0^-$, which is not changed from working cycle to working cycle. The change of system-pressure over time is measured and the system-pressure time derivative $D_0$, is calculated in step S110. The change of system-pressure over time is the inclination of the tangent, $D_{02}$, and $D_{02}$ is different from (inclination lower than) the derivative $D_{01}$. Said derivative value $D_{02}$ is then used in step S120 for calculating the target system-pressure time derivate value $D_{target}$ using Eq. 1.

The target system-pressure time derivate $D_{target}$ is then used in S130 for comparing system-pressure time derivative $D(t)$ to $D_{target}$ during the rise of system-pressure until $D(t)$ equals $D_{target}$. In step S140, target system-pressure $p_n^-$ is determined by measuring and selecting the measured value $p_n^-$ when $D(t)$ equals $D_{target}$ The time is indicated as $t=t_1$. The target system-pressure $p_n^-$ for $W_{C2}$ is essential lower than target system-pressure $p_n^-$ for $W_{C1}$. The maximum system-pressure S2H and a minimum system-pressure S2h is calculated in step S150 by means of the target system-pressure $p_n^-$, the pre-set system-pressure $p_0^-$ and the equations Eq. 1 and Eq. 2. In step S160, the vacuum generator arrangement is controlled and operated within an energy saving system-pressure interval defined by a maximum system-pressure S2H and a minimum system-pressure S2h. If the maximum system-pressure S2H and a minimum system-pressure S2h had been manually set, in-variable, and adapted to target-system pressures related to $W_{C1}$, a fluctuation of the system-pressure could result in a loss of the energy saving functionality.

The advantage of the invention over prior art is that the invention makes it possible to consider the fluctuation in system-pressure of the system and to determine by calculating the maximum system-pressure S2H and a minimum system-pressure S2h for each working cycle $W_C$ based on the determined target system-pressure $p_n^-$ and the pre-set system-pressure $p_0^-$. Thus, a maximum system-pressure S2H and a minimum system-pressure S2h are calculated based on the target system-pressure $p_0^-$ determined for the current working cycle $W_{Cn}$ (n=1, 2, 3, . . . ) and the pre-set system-pressure $p_0^-$. The maximum system-pressure S2H and a minimum system-pressure S2h for each working cycle $W_C$ is in this way adapted to fluctuations in system-pressure level in the measured system-pressure of the vacuum chamber of the vacuum gripper tool.

Figure 9:
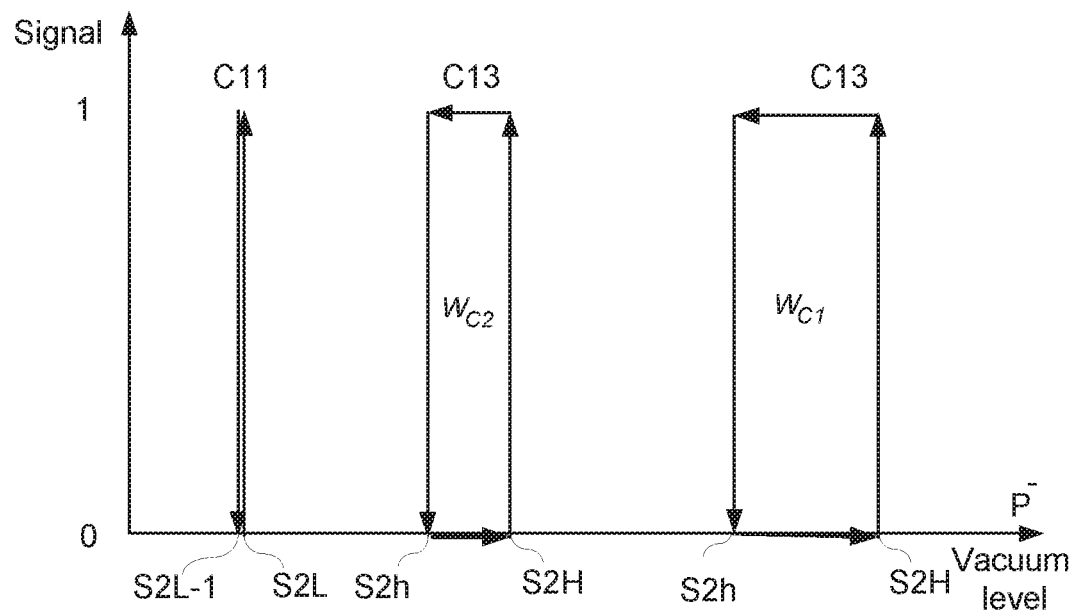
FIG. 9 is a diagram illustrating the vacuum based control signals C11 and C13 as a function of vacuum pressure.

FIG. 9 is a diagram illustrating the vacuum based control signals C11 and C13 as a function of system-pressure. C11 and C13 are vacuum level based control signals. The control signal C11 is defined between two system-pressure levels indicated as S2L-1 and S2L in the diagram. Said control signal C11 has already been described in the description text to FIG. 3.

The control signal C13 is defined between two system-pressure levels indicated as S2h and S2H. In the following example, the values of the signals C11 and C13 are binary, "one" or "zero". For any working cycle $W_C$, C13 is set to "1" during energy saving when the vacuum generation is "off" wherein the vacuum system pressure $p^-(t)$ is sinking from system-pressure S2H to S2h. C13 switches from "one" to "zero" when the vacuum system-pressure (t) is equal to or less than S2h. C13 remains as "zero" until the system-pressure $p^-(t)$ is equal to S2H, where C13 switches to "zero" and the vacuum generator is set "off". When the vacuum gripper tool is released, the system-pressure will sink rapidly to "zero".

As further is illustrated in FIG. 9, the closer the system-pressure of a working cycle $W_C$ is the vacuum system-pressure C11, the narrower pressure swing, i.e. allowed pressure band, between S2H and S2h is possible. Thus, the pressure swing for working cycle $W_{C1}$ is larger than for working cycle $W_{C2}$. This is due to the fact that target system-pressure $p_n^-$ for $W_{C2}$ is essential lower than target system-pressure $p_n^-$ for $W_{C1}$ and the distance between system-pressure C11 and target system-pressure $p_n^-$ decreases with decreasing target system-pressure $p_n^-$ allowing less pressure swing, which also is illustrated in FIG. 10.

Figure 10:
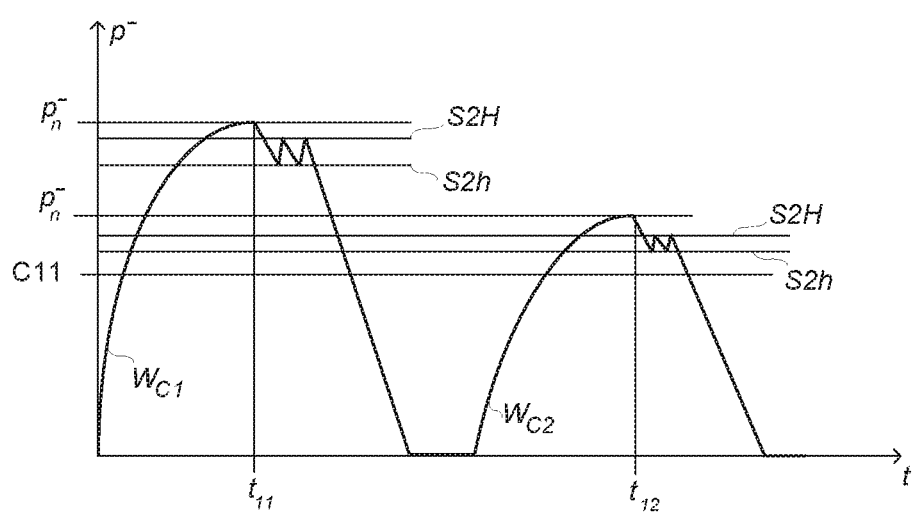
FIG. 10 is a pressure over time diagram illustrating the level adaptation to working cycles.

FIG. 10 is a pressure over time diagram illustrating working cycles for a vacuum gripper. Corresponding FIG. 4 is illustrating a problem that may occur during an operation process of a working station when the threshold values $ES_{Low}$ and $ES_{High}$ are set manually, wherein the setting is not adjusted to fluctuations of the vacuum generation and pressure during each working cycle $W_C$. The advantage of the invention over prior art is that the invention makes it possible to consider the fluctuation in system-pressure of the system and adapt the maximum system-pressure S2H and a minimum system-pressure S2h for each working cycle $W_C$ based on the determined target system-pressure $p_n^-$ and the pre-set system-pressure $p_0$. Thus, a maximum system-pressure S2H and a minimum system-pressure S2h are calculated based on the target system-pressure $p_n^-$ determined for the current working cycle $W_{Cn}$ (n=1, 2, 3, . . . ) and the pre-set system-pressure $p_0^- = C11$.

Other advantages compared to prior art is no waste and/or easy to use. Since typically, but without limitation thereto, only one system-pressure sensor 4 is used, there is no need for additional sensors and external functions. No sensors are needed on each vacuum gripper 6, for example suction cup, but only one centrally located, or centralized sensor as described above.

It is an advantage to locate the ADL function and method in the vacuum system controller (50 in FIG. 5) and not in the main controller (7 in FIG. 5). Said controllers are communicating with each other via bus wirings, e.g. cables. Said wiring often introduces delay due to the length of the wiring. Such a delay may be of substantial significance causing disturbance of the control and operation of the vacuum system. If the ADL function and method is located in the vacuum system controller, which is closer to the vacuum system than the main controller, said delay is eliminated.

The controller 50 or the inventive method requires no manual intervention or setting in order to be used. This is an advantage compared to prior art device often requiring intensive manual labor by the operator, or the operator setting control parameters having unnecessary long time periods to ensure proper venting to atmosphere. There is also no need for manual setting and calibration as the success of each cycle is evaluated and used automatically to improve performance.

An advantage with this embodiment is that, since the method S100 and vacuum system controller is continuously adapting, and is only activated for as often and as long as necessary dictated by the actual need of the application.

But, according to an alternative embodiment, or in addition, the vacuum system controller can be adapted so that the operator may also manually adjust the control parameters to better fit individual needs of an application or use.

The vacuum system-pressure $p^-(t)$ can be monitored continuously or periodically and fluctuation can be detected autonomously.

According to an embodiment, each previous release-cycle is analyzed and it's parameters re-evaluated autonomously.

The schematically illustrated vacuum generator 3 in FIGS. 1 and 5 is typically realized as an ejector. The vacuum gripper tool 6 may be realized as a suction cup, or as a set of suction cups that are commonly supplied from the vacuum generator 3.

It shall be noted that FIGS. 1 and 5 merely depicts the general layout of a vacuum system for the purpose of illustrating the invention, and that a vacuum system in practice can comprise additional valves, sensors and flow connections in order to adapt the vacuum system to a desired functionality, as would be known to a person skilled in the art.

The invention is defined in the accompanying claims, encompassing the above and other modifications of the invention which may be appreciated by the skilled person from the teachings provided above.

As an example, the components that define and/or operate the vacuum system controller in this example may be implemented by special-purpose software (or firmware) run on one or more general-purpose or special-purpose computing devices. Such a computing device may include one or more processing units, e.g. a CPU ("Central Processing Unit"), a DSP ("Digital Signal Processor"), an ASIC ("Application-Specific Integrated Circuit"), discrete analogue and/or digital components, or some other programmable logical device, such as an FPGA ("Field Programmable Gate Array"). In this context, it is to be understood that each "component" of the controller 5 refers to a conceptual equivalent of an algorithm; there is not always a one-to-one correspondence between components and particular pieces of hardware or software routines. One piece of hardware sometimes comprises different components. For example, the processing unit may serve as one component when executing one instruction, but serve as another component when executing another instruction. In addition, one component may be implemented by one instruction in some cases, but by a plurality of instructions in some other cases. The computing device may further include a system memory and a system bus that couples various system components including the system memory to the processing unit. The system bus may be any of several types of bus structures including a memory bus or memory controller, a peripheral bus, and a local bus using any of a variety of bus architectures. The system memory may include computer storage media in the form of volatile and/or non-volatile memory such as read only memory (ROM), random access memory (RAM) and flash memory. The special-purpose software may be stored in the system memory, or on other removable/non-removable volatile/non-volatile computer storage media which is included in or accessible to the computing device, such as magnetic media, optical media, flash memory cards, digital tape, solid state RAM, solid state ROM, etc. The computing device may include one or more communication interfaces, such as a serial interface, a parallel interface, a USB interface, a wireless interface, a network adapter, etc. One or more I/O devices may be connected to the computing device, via a communication interface, including e.g. a keyboard, a mouse, a touch screen, a display, a printer, a disk drive, etc. The special-purpose software may be provided to the computing device on any suitable computer-readable medium, including a record medium, a read-only memory, or an electrical carrier signal.

Typically, all the functions to operate the controller and method are included in one compact package.

The invention claimed is:

1. A method for automatic pressure level determination and adaptation enabling energy saving in working cycles in a vacuum system operating a vacuum gripper tool for transportation of objects, said vacuum system comprises a vacuum generator arrangement driven by a compressed air flow, wherein the vacuum generator arrangement via a vacuum chamber being part of the vacuum system is arranged to be brought in flow connection with the vacuum gripper tools, in order to supply vacuum to the vacuum gripper in result of the compressed air flow, wherein a pressure sensor for monitoring a system-pressure $p^-(t)$ is arranged inside the vacuum chamber; and a vacuum system controller being electrically connected to a main controller, wherein the vacuum system controller is arranged to control and communicate with the vacuum generator arrangement and communicate with the pressure sensor, and the vacuum system controller is arranged to monitor the measured system-pressure $p^-(t)$ continuously, wherein the vacuum system controller further is capable to calculate a system-pressure time derivative $D(t)=dp^-/dt$ during the working cycles, wherein the method comprises the steps of:

determining at start-up of a working cycle value $D_0$ of the system-pressure time derivative at a pre-set system-pressure $p_0^-$;

calculating value $D_{target}$ of target system-pressure time derivative using the value $D_0$;

comparing the system-pressure time derivative $D(t)$ to $D_{target}$ until $D(t)$ equals $D_{target}$;

determining a target system-pressure $p_n^-$ where $D(t)$ equals $D_{target}$;

calculating the maximum system-pressure S2H and the minimum system-pressure S2$h$ by means of the target system-pressure $p_n^-$ and the pre-set system-pressure $p_0^-$;

operating the vacuum generator arrangement to reestablish a vacuum system-pressure $p^-(t)$ to maximum system-pressure S2H when the vacuum system-pressure $p^-(t)$ is equal to or closely equal to the minimum system-pressure S2$h$.

2. The method according to claim 1, wherein the calculation of the value $D_{target}$ is performed by using the equation $$D_{target}=k*D_0,$$

wherein $0<k<1$.

3. The method according to claim 1, wherein the calculating step comprises calculating the maximum system-pressure S2H by $$S2H = p_0^- + (p_n^- - p_0^-) * K_1;$$

and the minimum system-pressure by $$S2h = p_n^- - (p_n^- - S2H) * K_2;$$

Where $K_1$ is set to a value $0.5 \leq K_1 \leq 1.0$ and $K_2$ is set to a value $0 \leq K_2 \leq 20$.

4. The method according to claim 1, wherein the operating step the vacuum generator arrangement is closed (off) if $p^-(t) > S2H$ and open (on) if $p^-(t) < S2h$.

5. The method according to claim 1, wherein the operating step the vacuum generator arrangement comprises an on/off valve that is closed (off) if $p^-(t) > S2H$ and open (on) if $p^-(t) < S2h$.

6. The method according to claim 1, wherein system-pressure $p^-(t)$ is monitored continuously and fluctuation is detected autonomously.

7. The method according to claim 1, wherein system-pressure $p^-(t)$ is monitored periodically and fluctuation is detected autonomously.

8. A controller for automatic pressure level determination and adaptation enabling energy saving in working cycles in a vacuum system operating a vacuum gripper tool for transportation of objects, said vacuum system comprises a vacuum generator arrangement driven by a compressed air flow, wherein the vacuum generator arrangement via a vacuum chamber being part of the vacuum system is arranged to be brought in flow connection with the vacuum gripper tools, in order to supply vacuum to the vacuum gripper in result of the compressed air flow, wherein a pressure sensor for monitoring a vacuum system-pressure $p^-(t)$ is arranged inside the vacuum chamber; and a vacuum system controller being electrically connected to a main controller, wherein the vacuum system controller is arranged to control and communicate with the vacuum generator arrangement and communicate with the pressure sensor, and the vacuum system controller is arranged to monitor the measured system-pressure $p^-(t)$ continuously, wherein the vacuum system controller further is capable to calculate a system-pressure time derivative $D(t) = dp^-/dt$ during the working cycles, said controller comprising a processor in a processing circuitry being operative to perform the steps of:

determining at start-up of a working cycle value Do of the system-pressure time derivative at a pre-set system-pressure $p_0^-$;

calculating value $D_{target}$ of target system-pressure time derivative using the value $D_0$;

comparing the system-pressure time derivative D(t) to $D_{target}$ until D(t) equals $D_{target}$;

determining a target system-pressure $p_n^-$ where D(t) equals $D_{target}$;

calculating the maximum system-pressure S2H and the minimum system-pressure S2h by means of the target system-pressure $p_n^-$ and the pre-set system-pressure $p_0^-$;

operating the vacuum generator arrangement to reestablish a vacuum system-pressure $p^-(t)$ to maximum system-pressure S2H when the vacuum system-pressure $p^-(t)$ is equal to or closely equal to the minimum system-pressure S2h.

9. The controller according to claim 8, wherein the calculation of the value $D_{target}$ is performed by using the equation $$D_{target} = k * D_0,$$

wherein $0 < k < 1$.

10. The controller according to claim 8, wherein the calculation of the maximum system-pressure S2H is performed by using the equation $$S2H = p_0^- + (p_n^- - p_0^-) * K_1;$$

and the minimum system-pressure (S2h) is performed by using the equation $$S2h = p_n^- - (p_n^- - S2H) * K_2;$$

Where $K_1$ is set to a value $0.5 \leq K_1 \leq 1.0$ and $K_2$ is set to a value $0 \leq K_2 \leq 20$.

11. The controller according to claim 8, wherein the vacuum generator arrangement is operated to close (off) if $p^-(t) > S2H$ and open (on) if $p^-(t) < S2h$.

12. The controller according claim 8, wherein the vacuum generator arrangement comprises an on/off valve which the vacuum generator arrangement is operated to the vacuum generator arrangement is operated to close (off) if $p^-(t) > S2H$ and to open (on) if $p^-(t) < S2h$.

13. The controller according to claim 8, wherein system-pressure $p^-(t)$ is monitored continuously and fluctuation is detected autonomously.

14. The controller according claim 8, wherein system-pressure $p^-(t)$ is monitored periodically and fluctuation is detected autonomously.

* * * * *